(12) United States Patent
Hirsch

(10) Patent No.: US 8,988,687 B2
(45) Date of Patent: Mar. 24, 2015

(54) MATRIX FOR DETECTION/ANALYSIS OF RESIDUES

(75) Inventor: Israel Hirsch, Herzelia (IL)

(73) Assignee: Aphelion Ltd., Herzelia (IL)

( * ) Notice: Subject to any disclaimer, the term of this patent is extended or adjusted under 35 U.S.C. 154(b) by 651 days.

(21) Appl. No.: 12/741,279

(22) PCT Filed: Nov. 3, 2008

(86) PCT No.: PCT/IL2008/001439
§ 371 (c)(1),
(2), (4) Date: May 4, 2010

(87) PCT Pub. No.: WO2009/060428
PCT Pub. Date: May 14, 2009

(65) Prior Publication Data
US 2010/0238447 A1 Sep. 23, 2010

(30) Foreign Application Priority Data
Nov. 6, 2007 (IL) .......................... 187203

(51) Int. Cl.
| G01N 21/00 | (2006.01) |
| G01N 31/22 | (2006.01) |
| G01N 21/84 | (2006.01) |
| G01N 1/22 | (2006.01) |
| G01N 21/78 | (2006.01) |
| G01N 21/77 | (2006.01) |
| G01N 15/06 | (2006.01) |

(Continued)

(52) U.S. Cl.
CPC ............ G01N 31/22 (2013.01); G01N 21/8483 (2013.01); G01N 1/2208 (2013.01); *G01N 21/783* (2013.01); *G01N 2021/7796* (2013.01); *G01N 15/0637* (2013.01)

USPC .......................................... 356/437

(58) Field of Classification Search
CPC . G01N 21/39; G01N 21/3504; G01N 21/031; G01N 2021/399; G01J 3/42
USPC ................................. 356/437–442
See application file for complete search history.

(56) References Cited

U.S. PATENT DOCUMENTS

| 2005/0070025 A1 | 3/2005 | Mooradian et al. |
| 2008/0008625 A1* | 1/2008 | Thomas et al. ............ 422/82.05 |
| 2008/0138911 A1* | 6/2008 | Robins .......................... 436/167 |

FOREIGN PATENT DOCUMENTS

| GB | 2 261 949 A | 6/1993 |
| WO | 2006/038028 A1 | 4/2006 |
| WO | 2006/061607 A1 | 6/2006 |
| WO | 2007/008236 A2 | 1/2007 |

OTHER PUBLICATIONS

The International Search Report for International Application No. PCT/IL2008/001439, two pages, mailed Apr. 6, 2009.

* cited by examiner

*Primary Examiner* — Tarifur Chowdhury
*Assistant Examiner* — Md Rahman
(74) *Attorney, Agent, or Firm* — Vorys, Sater, Seymour and Pease LLP; Susanne M. Hopkins

(57) ABSTRACT

Provided is a device and method for detecting the presence of a material in a gaseous medium, including a reaction assembly including at least one detection unit including a matrix adapted for exposure to the gaseous medium, such that at least part of the gaseous medium comes into contact with the matrix; the matrix being configured for capturing a gas-born particle of a material carried by the gaseous medium, and for permitting a liquid or solute reagent to come in contact with the matrix, thereby enabling said liquid reagent to react with said particle to yield an optically altered reaction product.

25 Claims, 1 Drawing Sheet

MATRIX FOR DETECTION/ANALYSIS OF RESIDUES

This is a National Phase Application filed under 35 U.S.C. 371 as a national stage of PCT/IL2008/001439, filed Nov. 3, 2008, the content of which is hereby incorporated by reference in its entirety.

FIELD OF THE INVENTION

This invention relates to a matrix and a method for the detection and/or analysis of residual materials, e.g., contaminants, in a gaseous medium such as air or on the surface within said environment.

BACKGROUND OF THE INVENTION

The development of detection techniques for real-time detection of particles, such as air-borne or environmental contaminants, has been a major task of industries, such as the chemical industries, as well as national authorities attempting to control the evolution of borne contaminants. As a result of industrial processing of materials, fine particulates are generated which may be harmful to both humans and animals in the surrounding environment. With the increase in public demand for a cleaner and safer environment, the industries have been seeking low cost and handy devices that would be effective in providing real-time indication to the presence of such particulates, an indication which would initiate an immediate corrective and/or preventive response and/or further analysis and quantification.

Due to the usually low concentration of contaminants in the air, particularly at the on set of contamination, sampling devices, particularly those suitable for air sampling or for collection of residual contaminants from any one surface being in possible contact with the contaminants, have traditionally operated on the basis of sampling the environment for such particulates for later analysis, employing high sensitivity detection systems which are usually stationary, expensive and require skilled personnel for operation. Although numerous real-time detection methods of such particulate contaminants are known, they remain expensive and due to their complexity require the involvement of skilled operators.

It is therefore most desirable to have a device that is capable of providing almost instantaneous warning of the existence of contaminating particulates in the environment, e.g., in the air or on surfaces contained therein, at the lowest possible concentration, namely at the very onset of contamination, so that the individual may take steps to stop the contamination and/or avoid further exposure.

SUMMARY OF THE INVENTION

The inventor of the present invention has now developed a simple, low cost and real-time device for determining the presence of a microscopic particle of a material. The basic principle of the device of the invention is the sampling and analysis of a particulate matter on a suitable substrate contained within the device. The substrate, not only allows the capturing of a single or a plurality of such particles, but also allows the analysis thereof by a great variety of analytical methods, particularly those which do not necessitate the employment of high cost and complex methodologies.

Thus, in one aspect of the present invention there is provided a device for detecting the presence of a material in a gaseous medium, said device comprising a reaction assembly comprising at least one detection/analysis unit each of said at least one detection/analysis units comprising a matrix located to be exposed to the gaseous medium flow such that at least part of the gaseous medium comes into contact with the matrix; the matrix being configured for capturing a gas-borne particle of a material carried by the gaseous medium, and for permitting a liquid or solute reagent to flow through elements of the matrix, thereby enabling said liquid reagent to react with said particle to yield an altered reaction product.

When the device is placed in a volume of gas or in the path of a gas flow, gas-borne particles, being of any size, in some embodiments being microparticles and in others nanoparticles, or particles of similar or different sizes contained within the volume are captured (in some embodiments by physical interaction) by the surface of the matrix. The matrix is typically an array of spaced-apart elements arranged and made of at least one selected material which allows the capturing of the gas-borne particle(s). In some embodiments, the elements are arranged as a one- or two- or three-dimensional array. In other embodiments, the one or two or three-dimensional array is an array of the elongated elements, which maybe parallel to each other, arranged as a grid or in a warp and weft pattern. In other embodiments, the matrix is formed by spaced-apart elements defined by a loosely laid wire-like continuous member. Alternatively, the matrix is formed by spaced-apart elements defined by loosely laid plurality of wire-like members.

In some embodiments, the matrix is made of a fibrous, or in other embodiments microfibrous material, which is selected to permit a liquid or solute reagent to flow through it, and thereby react with the particle captured by the matrix.

The matrix material is selected in a non-limiting manner from materials such as cross-linked porous polymers, porous inert hydrophilic polymers, synthetic or non-synthetic textile fibers, non-woven staple or continuous fibers, cotton, wood fibers, cellulose, vegetable fibers, animal fibers, and micro tube like yarns of the materials. The matrix material is different from paper or paper products. The matrix material is typically (but not necessarily) chosen to be colorless or white to the naked eye, or of a different light color.

The material is additionally chosen to have an overall large surface area so as to increase chances of particles coming in contact with and being arrested by the matrix. As a person skilled in the art will appreciate, the greater surface area of the material making up the matrix, the greater the probability that at least one particle will be captured on it. Therefore, the matrix is typically structured as a coarse surface having regions of large surface area. Where, for example, the matrix material is cotton, the cotton fibers may be woven as a grid-like structure, with the cotton fibers or microfibers being in intimate proximity to each other. Such a configuration provides a matrix with a high density of capture sites.

The capability of the matrix to hold a particle present in a gaseous medium may be enhanced by arranging the matrix on top of a substrate layer of an adhesive material (not shown), for example acrylic based. This arrangement further ensures that the particle is held on the matrix. The substrate layer is selected to be stable and unreactive under the conditions employed, e.g., conditions associated with detection and/or analysis.

Upon capture, the matrix is washed with a liquid or solute reagent which is capable of reacting with the particles. As a person skilled in the art would realize, the washing technique is selected so as to introduce sufficient liquid or solute reagent to the matrix without causing the particle captured thereon from detaching. The reagent may be presented to the matrix from a feeding unit within the device or from an external reservoir, from which it is added drop wise, sprayed or by any other method as may be known to a user. Once the reagent is added, it reacts with the particle captured on the matrix, or with any material associated therewith and which may or may not be physically attached thereto (i.e., to the particulate matter) thereby producing a product with measurable characteristics, e.g., optical, which are different from those of either the particle captured or the reagent used. In the absence of a particle, or a plurality thereof, a product having an altered measurable characteristic will not be obtained.

Where the altered measurable characteristic of the product is optical, the measurable characteristic may be, for example, altered light absorbent, light reflective or light transmission properties, which may be visible to the naked eye and/or which may require additional analytical measurements such as spectroscopic tools for characterization.

Without wishing to be bound by theory, when the liquid reagent reacts with the particle on the matrix, or with a material associated therewith (such as a material also captured by the matrix from the same airflow) the resulting altered reaction product migrates from the location on the matrix where the particle is situated via, e.g., capillary forces to adjacent locations on the matrix. The migration through the matrix causes an enhancement of the altered effect, e.g., optical effect, as the altered optical picture is now distributed over a larger surface of the matrix and not immediately surrounding the particle.

This enhanced effect allows the detection of individual particles, for example microparticles.

The material to be detected and/or analyzed is selected from air-borne powders, dust, pollen, mold spores, smoke particles, combustion residues, explosive residues, particulate emissions from volatile or unstable solids or surfaces, particulate emissions from humans and objects, drug residues and any other type of material.

These material particulates may be detected and/or analyzed as individual particulates or as a plurality thereof, depending on the number of the particles which are captured on the matrix. A typical residual particulate may be as small as 0.1 to 1000 micron in diameter, or weigh as little as $10^{-15}$ gram to 1 milligram in weight.

The particulate material may be carried by or contained in any gaseous medium such as pure gases, mixture of gases, gases of combustion, gases emitted from volatile solids or materials, gases emitted from the surface of an object or an animal, e.g., human or non human, and air.

Additionally, where the particles to be detected and/or analyzed are suspected to be on a surface, the surface may be treated, for example by wiping, scratching, or any other way to allow particles to detach from the surface and be captured by the matrix.

In some embodiment, the particles are carried in a gaseous medium and in a further embodiments, the medium is air.

For the device to come into contact with gas-borne particles of a material to be detected, it must be accommodated at the pathway of the flow of the gaseous medium containing the particle(s) or within the gaseous medium, or in some embodiments be placed in a sampling compartment containing the gaseous medium. Where the flow of the gaseous medium is directional, the device may be placed substantially facing the flow, in some embodiments perpendicular thereto, in such a way that a particle can enter the device and be captured by the matrix.

Alternatively, the device may be manipulated, for example, by moving it side to side or at any direction so as to induce movement of gas (air) near the matrix and the lift up of particles within the gas. Where it is desirable, the particles may be agitated so as to be gas-borne by employing a fan or a gas-circulating device. Such circulation may be sufficient to agitate the gas volume and cause the particles contained therein to be liberated into the gas stream.

It is desirable at times to detect and/or analyze the presence of contaminating particles such as drugs and explosives on the surfaces of objects such as packages, luggage, and clothing or even on humans and animals and/or their belongings. Drug or explosive particles may be loosen from the outer surfaces of such objects (or inner surfaces by opening and exposing the internal surfaces to the sampling process) or even released from within them when air stream is employed to agitate the surface, as well as the air surrounding it, in the presence of the device. Once the particles are loosen and lifted into the air surrounding the device, they may be captured by the fibrous matrix. This is highly beneficial where drugs and explosives are concerned as particles originating from such chemicals or chemical compositions have sticky ends. Any surface in contact with such particles will readily become contaminated with them and thus their presence may be detected.

As a great variety of materials may be detected by the device of the invention, the liquid or solute reagent may be one chosen based on the specific environment, the suspected contaminants, their concentration, the specific matrix used and other parameters which are readily known to a person skilled in the art. The detection and/or analysis may be any one of: (i) verification as to the presence of at least one particle, (ii) qualitative analysis of the at least one particle, and/or (iii) quantitative analysis of the at least one particle vis-à-vis other particles or as a concentration thereof in the tested medium. In some embodiments, the liquid reagent is to provide a yes/no answer, where "yes" indicates the presence of at least one particle (e.g., generally or of a particle belonging to a specific type or family of materials) and "no" indicates that no particle (or no particle of a specific composition or belonging to one or other group) was trapped by the matrix.

Alternatively, the liquid reagent may be selected to be capable to react with a group of materials (a family of materials) and produce an altered, e.g., optical product which is indicative of the family as a whole. Such altered optical reaction may be in response to the presence of a signature molecule common to the family of materials or to the presence of a chemical moiety which is common to each of the molecules in the family.

In some embodiments, the liquid reagent is selected to identify a sub-group of materials or a specific compound within that group.

Typically, the reagent is one which is capable of reacting with the particles of the material. Where the particles are of a mixture of materials such as organic and inorganic materials, the liquid reagent is selected to react with any one component of the mixture. As typically the identity and chemical composition of the particles is unknown, the reagent may be a mixture of numerous reagents, wherein each of the reagents can undergo a separate reaction with the particle and result in an optically altered product. In such a case, the optical end result differs from the optical characterization of any one of the reagents used in the mixture.

It should be understood that where the reagent is a liquid or a solid, it should be dissolved in an appropriate solvent or absorbed or otherwise applied to the matrix in a liquid form, e.g., as a liquid reagent or as a solution comprising it. The solvent used for dissolving the reagent may be organic such as DMSO, an alcohol (methanol, ethanol, etc., or mixtures thereof), an ether, a ketone, and others, and mixtures thereof;

aqueous media optionally containing a salt, an acid, a base, an alcohol, a colorant and/or other additives; or any combination thereof.

For example, for the presumptive detection of polynitro aromatics, nitrate esters and nitramines a binary system containing (a) an alcoholic or alkaline solution such as a tetraalkyl ammonium hydroxide salt, and (b) a color-forming reagent, may be used. The color-forming reagent may comprise a single liquid reagent of a single component or a liquid reagent made of more than one component.

Non-limiting examples of color-forming reagents are 4-aminobenzoic acid, 4-aminoacetophenone, diaminodiphenylsulfone, 4-aminobenzonitril, procain, sulfanilamide, N-phenyl-1-naphthylamine, N-phenyl-1-naphthylamine, N,N-dimethyl-1-naphthylamine and N-1-naphthylethylenediamine.

In some embodiments, the reagent(s) is dispensed onto the matrix only after a particle has been captured on the matrix. In further embodiments, the matrix is pre-rinsed or absorbed with a component of the reagent which may also be in the solid form. Such pre-treatment has in some embodiments, the ability to provide, upon contact with a particle, an initial (e.g., color) indication to its presence on the matrix. Based on the initial indication, a reagent may be selected so as to qualitatively determine the identity of the material particulate on the matrix.

Depending on the size of the matrix, the amount or volume of the liquid or solute reagent may vary. A person skilled in the art would have the ability to determine based on such parameters as the specific application and size of the device the amount of reagent used. In some embodiments, the reagent is added in microliter amounts.

In another embodiment, the device further comprises a plurality of detection units that can be brought into the reaction zone in which the member-associated matrix is exposed to permit the capture of the particles. In some embodiments, the device comprises a strip carrying the reaction assembly with a plurality of detection units being arranged in a spaced-apart relationship along the strip and being successively brought into and out of the reaction zone by longitudinal movement of the strip.

The strip may be included within a cassette, which in some embodiments defines a storage zone for storing unused detection units and a receiving zone for receiving used detection units and has an opening defining the reaction zone for accommodating therein the detection unit matrix.

Alternatively, the unused detection units may be stored at a storage zone outside of the device. A receiving zone situated within the device may receive used detection units for storage until such a point where the used detection units are discarded by the user, or for immediate discarding of a just-used detection unit.

As stated above, the presence of the (optically) altered product may be determined by any analytical method including spectroscopic analysis. In some embodiments, the detection (and/or analysis) is carried out at ambient (namely, at a temperature between 25 and 27° C.). In some further embodiments, the detection (and/or analysis) is carried out at a temperature above or below ambient. In further embodiments, the detection (and/or analysis) is carried out at a pressure above or below 1 atm. In still other embodiments, the detection (and/or analysis) is carried out in vaccuo.

In some embodiments, the detection (and/or analysis) is carried out by the naked eye. In some other embodiments, the detection (and/or analysis) is by the use of a magnifying glass or a light or electronic microscope.

The spectroscopic analysis may be in any one or more of the following spectral ranges: X-Ray, ultraviolet (UV), visible, near infrared (NIR), short wave infrared (SWIR), mid-infrared (MIR), far-infrared (FIR), TH (terahertz) and MM (millimeter) spectral waves, and by utilizing one or more methods employing radioactive materials (or sources). The spectrometer may operate to collect images based on the following detection modalities: X-Ray, UV, visible, near-IR (NIR), short wave infrared (SWIR), mid-IR (MIR), far-IR (FIR), TH (terahertz), MM (millimeter) spectral waves/energies; absorption imaging in either transmission and/or reflectance modes; Raman scatter imaging; fluorescence; photoluminescence; chemiluminescence; and electroluminescence imaging and/or any combination of these methods/technologies.

Typically, as the reaction between a particle of the material and the reagent takes a short time from the application of the reagent to complete, the presence of the particle on the matrix may be determined in real-time. The device of the present invention has demonstrated that a qualitative signal, sufficient to visually observe the optical change, may be observed—at room temperature—in as short as a few seconds, e.g., between 2 and 10 seconds, after application of the liquid reagent.

In some embodiments, the particle density required for determining the presence of a particle on the matrix and thus in the tested gaseous medium, is between 1 and 20 particles. In other embodiments, the particle density is 1 particle on the matrix.

In another aspect of the invention, there is provided a hand-held device for detecting the presence of a material in a gaseous medium, the device comprising a body part having a reaction zone exposed to a flow of the gaseous medium; and a reaction assembly comprising a plurality of detection units and movable with respect to the reaction zone so as to successively accommodate each of the detection units to be used at the reaction zone and move the used detection unit from the reaction zone, the detection unit comprising a matrix configured for capturing a gas-borne particle of a material to be detected and carried by the gaseous medium, and for permitting a liquid or solute reagent flow through elements of the matrix, the device thereby enabling a reaction between said liquid or solute reagent and the particle to yield an optically altered reaction product.

In yet another aspect of the invention there is provided a process for use in detection of the presence of a material in a gaseous medium, said process comprising:

(a) providing a matrix configured for capturing one or more gas-borne particles carried by the gaseous medium and for permitting a liquid or solute reagent to contact the elements of the matrix;

(b) causing the gaseous medium to contact the matrix; and (c) adding a liquid or solute reagent onto the matrix, said liquid or solute reagent being selected for reacting with said gas-borne particle(s), thereby yielding an optically altered reaction product and enabling its detection.

In some embodiments, the process comprises:

(a) bringing into position a matrix configured for capturing one or more gas-borne particles carried by the gaseous medium and for permitting a liquid or solute reagent flow through elements of the matrix;

(b) causing a gaseous medium to come into contact with the matrix;

(c) adding a liquid or solute reagent onto the matrix, said liquid or solute reagent being selected for reacting with the gas-borne particles, thereby yielding an optically altered reaction product;

(d) detecting said product; and (e) bringing into position another matrix and repeating steps (a)-(e).

The process of the invention, as detailed above, may be used to detect and/or analyze a single particle on the matrix. The detection method of particles which presence may be of risk to the operator of the device, such as in the case of hazardous chemical material particulates, can be conducted at any safe distance away from the surface or gaseous medium provided that a volume of gas from the vicinity of the surface or from the medium can be in gas communication with the device of the invention. With such an operational availability, the risk of exposure to hazardous agents to the operator is significantly reduced.

Implementation of the process and device of the present invention involves performing or completing selected tasks or steps manually, automatically, or a combination thereof. Moreover, according to embodiments of the process and device of the invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the process and device of the invention could be described as being performed by a data processor, such as a computing platform for executing a plurality of instructions.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF EMBODIMENTS

Figure 1:
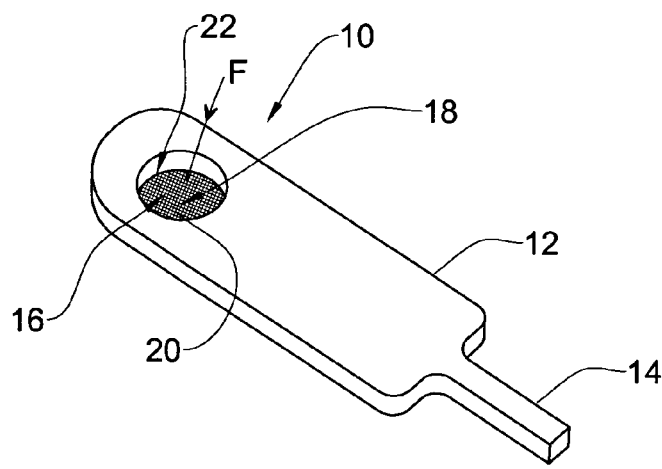
FIG. 1 is a schematic illustration of a hand-held device of the present invention.

Referring to FIG. 1, there is illustrated an example of a device 10 of the invention for detecting the presence of a material in a gaseous medium. The device 10 is configured as an exemplary device unit, in this case a hand-held unit having a body part 12 and a handle part 14. It should be appreciated however that the device 10 may be of any other desired shape and configuration. The body part 12 has a defined reaction zone 16 serving for accommodating therein a detection unit 18 of reaction assembly. In the present example, the reaction zone is constituted by an opening 20 made in the body part 12. The detection unit according to this example is disposable, and the reaction assembly is constituted by a set of such detection units. Generally, the detection unit can be configured so as to be removably installable within the opening, so as to enable replacement of the used detection unit by a new one. In some embodiments, however, the reaction assembly includes a carrier having a plurality of detection units enabling successively moving a detection unit to be used into and out of the reaction zone. This will be exemplified specifically further below with reference to FIG. 2.

The detection unit 18 is a matrix of spaced-apart elements 22 which are configured for capturing gas-borne particle(s) of a material to be detected carried by the gaseous medium.

Also, the matrix is made of a material permitting a liquid or solute reagent to substantially absorb and flow therethrough. These may for example be cotton fibers. Generally, the matrix elements may be arranged in a one- or two- or three-dimensional array, e.g., an array of intersecting elongated, wire- or fiber-like elements, or may be constituted by spaced-apart regions of a loosely laid wire. In the non-limiting example of FIG. 1, the matrix is in the form of intersecting cotton fibers defining a grid.

The detection unit 18 while being accommodated in the reaction zone 16 is exposed to a flow F of the gas medium. The flow of the gas medium may be provided by means of a natural air flow; or intentionally induced air flow, e.g., by moving the device or device body or by creation of a directional air flow towards the reaction zone.

According to another example, the flow of the gas medium possibly containing the particles of material to be captured by the matrix may be induced by patting on, scraping or scratching the surfaces of articles such as travel equipment, clothing, skin etc.

Thus, the provision of the gas medium flow towards the reaction zone results in the particles' adhesion (capture) by the elements of the matrix of the detection unit exposed to said flow. Then, the liquid or solute reagent flow is supplied onto and/or through the matrix elements (e.g. by dripping and/or spraying and/or dipping). This can be implemented using an internal or external to the device reagent supplier (reservoir), which is not specifically shown. The liquid or solute reagent is selected to react with a specific material. The presence of the liquid or solute reagent on the matrix elements induces a reaction between the captured particles and the reagent results in an optically altered reaction product. The latter is indicative of the presence of the particle(s) of a specific material in the gaseous medium in the surroundings of the device.

Figure 2A:
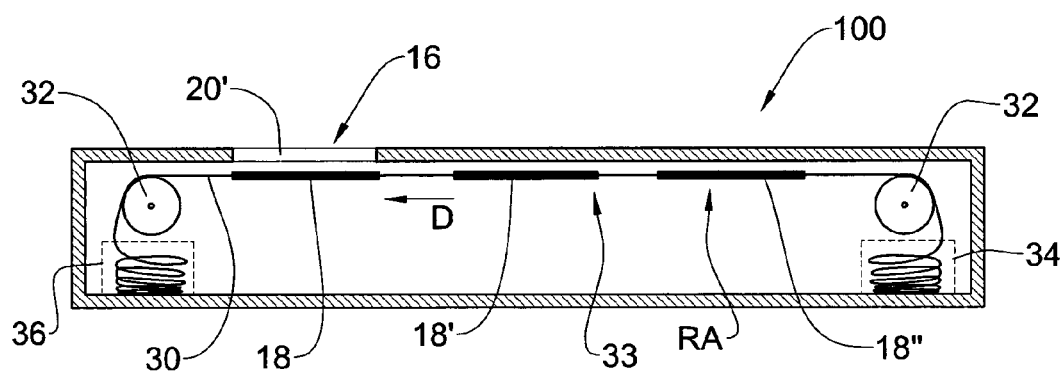
FIGS. 2A and 2B show two examples, respectively of a configuration of a reaction assembly suitable to be used in the device of the present invention.

Reference is now made to FIG. 2A showing a specific but non-limiting example of a reaction assembly RA suitable to be used in the device of the present invention. The reaction assembly is contained in a cassette 100, which may be constituted by the device body part (e.g., 12 in FIG. 1) or may be detachably attachable to the device body part. The cassette 100 is formed with an opening 20' which is aligned with the opening in the device body. The reaction assembly has a carrier 30 carrying a plurality of detection units—three such units (matrices) 18, 18' and 18" being shown in the present example. The carrier 30 is displaceable with respect to the opening 20' so as to successively pass each one of the detection units through the reaction zone defined by the opening 20'. In the present example, the detection units in the form of matrices described above are arranged in a spaced-apart relationship along the carrier. It should however be understood that generally this can be achieved by making the entire carrier in the form of a grid displaceable with respect to the reaction zone thus selectively bringing each one of successive regions of the carrier-grid at the reaction zone.

In the present example, the carrier 30 is a flexible strip, e.g. made of a fabric or plastic material, extending between guiding rollers 32 and kept under tension within a region 33 between the rollers, by a suitable arrangement (not shown) to move with respect to the reaction zone 20' in a general direction of the arrow D. Two ends of the strip outside the region 33 may be folded in a serpentine like fashion (or may be rolled up) within a storage zone 34 for storing unused detection units (before entering region 33) and a receiving zone 36 for receiving used detection units (after passage through region 33). It should be understood that the strip 30 may be movable along the device body or across it, providing it passes through the reaction zone by its successive regions.

Figure 2B:
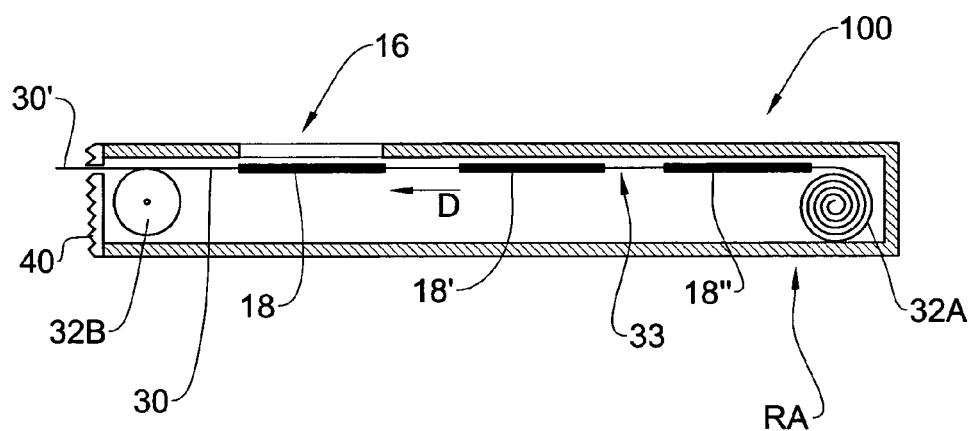

FIG. 2B shows another specific but not limiting example of the implementation of the reaction assembly RA. Similarly to the description of FIG. 2A, the reaction assembly may or may not be accommodated in a separate cassette 100. The reaction assembly RA is of the kind described in FIG. 2A, namely including a flexible strip-carrier 30 that has a plurality of detection unit regions which are successively brought to and out of the reaction zone 16 by the movement of the strip 30. In this example however, the detection unit after being used is pulled out of the device mechanically, e.g. pulled by the user, by pulling the strip by its end 30' projectable from the device (through an appropriate opening). This is implemented by winding the strip on a roller 32A and stretching the strip portion between this roller 32A and another guiding element (e.g. roller) 32B. Rotation of the roller 32A is initiated by pulling of the free end 30' of the strip, thus enabling to successively bring each detection unit to the reaction zone. The detection unit after being used becomes located at the strip portion outside the device body and can thus be detached. To this end, the device may be appropriately provided with a sharp-edge element 40. Alternatively, the strip may be transversely perforated at predetermined locations such as to ease detachment thereof.

The detection unit after being used is inspected to determine the presence and nature of the particles on the matrix. To this end, any known inspection tool may be used, being of the kind capable of carrying out material identification, e.g. visual, imaging or spectroscopic methods.

Those skilled in the art to which this invention pertains will readily appreciate that numerous changes, variations and modifications can be made without departing from the scope of the invention, mutatis mutandis.

The invention claimed is:

1. A device for detecting one or more materials borne in a gaseous medium, the device comprising:
a reaction assembly comprising at least one detection unit comprising a matrix configured to physically capture said one or more materials in particulate form, said one or more materials having a particle size between about 0.1 and 1000 micrometers from a flow of said gaseous medium, and configured to permit a liquid or solute reagent to come in contact with the matrix, thereby enabling said liquid or solute reagent to react with said one or more materials of particulate form to yield an optically altered reaction product.

2. The device according to claim 1, further comprising a liquid or solute reagent feeding unit for feeding the liquid or solute reagent onto the matrix.

3. The device according to claim 1, wherein said matrix is an array of spaced-apart elements arranged and made of at least one selected material allowing said capturing of the one or more materials in particulate form and said liquid or solute reagent to contact the matrix.

4. The device according to claim 3, wherein said elements are arranged in a one or two-or three-dimensional array of elongated elements, said elements being optionally intersecting to define a grid.

5. The device according to claim 4, wherein said matrix is made of a fibrous material.

6. The device according to claim 5, wherein said matrix is selected from cross-linked porous polymers, porous inert hydrophilic polymers, synthetic or non-synthetic textile fibers, non-woven staple or continuous fibers, cotton, wood fibers, cellulose, vegetable fibers, animal fibers, and micro tube like yarns of the materials.

7. The device according to claim 6, wherein said matrix comprises cotton fibers.

8. The device according to claim 1, wherein the liquid or solute reagent is selected to produce an altered reaction product having an altered measurable characteristic.

9. The device according to claim 8, wherein the altered measurable characteristic is an optical characteristic selected from light absorbent, and/or light reflective and/or light transmission properties.

10. The device according to claim 1, wherein said one or more materials in particulate form are selected from air-borne powders, dust, pollen, mold spores, smoke particles, combustion residues, explosive residues, particulate emissions from volatile or unstable solids or surfaces, particulate emissions from humans and objects, and drug residues.

11. The device according to claim 1, being configured to allow its movement by a user to thereby induce the flow of the gaseous medium onto the matrix.

12. The device according to claim 1, further comprising a reaction zone for accommodating the at least one detection unit therein.

13. The device according to claim 12, wherein said reaction zone is defined by an opening made in a device body.

14. The device according to claim 12, wherein the reaction assembly is configured for selectively bringing the detection unit to the reaction zone to thereby expose the member-associated matrix to the gaseous medium flow and permit the capture of the one or more materials in particulate form thereon.

15. The device according to claim 14, further comprising a strip carrying the reaction assembly comprising a plurality of detection units arranged in a spaced-apart relationship along the strip and being successively brought into and out of the reaction zone by longitudinal movement of the strip.

16. The device according to claim 15, wherein said strip is included within a cassette.

17. The device according to claim 16, wherein the cassette defines a storage zone for storing unused detection units and a receiving zone for receiving used detection units and has an opening defining the reaction zone for accommodating therein the detection unit matrix.

18. The device according to claim 12, further comprising a storage zone for storing unused detection units, and a receiving zone for receiving used detection units.

19. A process for detecting one or more materials borne in a gaseous medium, said process comprising:
(a) providing a matrix configured for capturing the one or more materials in particulate form, said one or more materials having a particle size between about 0.1 and 1000 micrometers, borne in the gaseous medium and for permitting a liquid or solute reagent to contact the matrix;
(b) causing the gaseous medium comprising the one or more materials in particulate form to contact the matrix, thereby said one or more materials in particulate form being captured by the matrix;
(c) adding the liquid or solute reagent onto the matrix, said liquid or solute reagent being selected for reacting with the one or more materials in particulate form, thereby yielding an optically altered reaction product and enabling its detection; and
(d) detecting the optically altered reaction product.

20. The process according to claim 19, further comprising:
after said step of providing, bringing the matrix into position; and
after said step of detecting, bringing into position another matrix and repeating steps (a)-(d).

21. A device for detecting one or more particulate materials carried by a gaseous medium, the device comprising:
   a reaction assembly comprising at least one detection unit comprising a matrix configured to physically capture said one or more particulate materials, said one more ore particulate materials having a particle size between about 0.1 and 1000 micrometers, from a flow of said gaseous medium, and configured to permit a liquid or solute reagent to come in contact with the matrix, thereby enabling said liquid or solute reagent to react with said one or more particulate materials to yield an optically altered reaction product,
   wherein the particulate material and the gaseous medium are different.

22. The device of claim 21, wherein the particulate material comprises nanoparticles or microparticles.

23. A process for detecting one or more particulate materials carried by a gaseous medium, comprising:
   (a) providing a matrix configured for capturing the one or more particulate materials, said one more ore particulate materials having a particle size between about 0.1 and 1000 micrometers, carried by the gaseous medium and for permitting a liquid or solute reagent to contact the matrix, wherein the particulate material and the gaseous medium are different;
   (b) causing the gaseous medium comprising the one or more particulate materials to contact the matrix, thereby the one or more particulate materials being captured by the matrix;
   (c) adding the liquid or solute reagent onto the matrix, the liquid or solute reagent being selected for reacting with the one or more particulate materials, thereby yielding an optically altered reaction product and enabling its detection; and
   (d) detecting the optically altered reaction product.

24. The process according to claim 23, further comprising:
   after said step of providing, bringing the matrix into position; and
   after said step of detecting, bringing into position another matrix and repeating the steps (a)-(d).

25. The process of claim 23, wherein the particulate material comprises nanoparticles or microparticles.

* * * * *